(12) United States Patent
Schmidt

(10) Patent No.: US 7,214,654 B1
(45) Date of Patent: May 8, 2007

(54) AGENT FOR THE MANUFACTURE OF BIOLOGICAL PARTS INCLUDING AN ACTIVE INGREDIENT COMPLEX AND CARRYING MATERIALS SUITABLE FOR THE ACTIVE INGREDIENT COMPLEX

(76) Inventor: Karlheinz Schmidt, Aeussere Weilest, 12, Gomaringen 72810 (DE)

( * ) Notice: Subject to any disclaimer, the term of this patent is extended or adjusted under 35 U.S.C. 154(b) by 0 days.

(21) Appl. No.: 09/295,302

(22) Filed: Apr. 21, 1999

Related U.S. Application Data

(63) Continuation-in-part of application No. 08/899,270, filed on Jul. 23, 1997, now Pat. No. 5,928,635, which is a continuation-in-part of application No. 08/313,113, filed on Dec. 7, 1994, now abandoned, which is a continuation-in-part of application No. 08/350,666, filed on Dec. 7, 1994, now Pat. No. 5,932,207.

(30) Foreign Application Priority Data

Sep. 17, 1992 (WO) .................................. 91/07324

(51) Int. Cl.
A61K 38/16 (2006.01)
A61K 38/18 (2006.01)

(52) U.S. Cl. .......................... 514/2; 530/350; 530/356; 424/422; 424/484

(58) Field of Classification Search .................... 514/2; 530/350, 356; 424/422, 484
See application file for complete search history.

(56) References Cited

U.S. PATENT DOCUMENTS

| | | | |
|---|---|---|---|
| 4,294,753 A | 10/1981 | Urist | |
| 4,472,840 A | 9/1984 | Jefferies | |
| 4,642,120 A | 2/1987 | Nevo et al. | |
| 4,703,108 A | 10/1987 | Silver et al. | |
| 4,832,686 A | 5/1989 | Anderson | |
| 4,919,666 A | 4/1990 | Buchhorn et al. | 623/16 |
| 4,932,973 A | 6/1990 | Gendler | |
| 4,950,483 A | 8/1990 | Ksander et al. | |
| 5,024,841 A | 6/1991 | Chu et al. | |
| 5,092,896 A * | 3/1992 | Meui et al. | 623/21 |
| 5,139,424 A | 8/1992 | Yli-Urpo | |
| 5,456,717 A | 10/1995 | Zweymüller et al. | 623/16 |
| 5,545,208 A | 8/1996 | Wolff et al. | 623/1 |
| 5,769,897 A * | 6/1998 | Harle | 623/16 |
| 5,824,651 A | 10/1998 | Nanci et al. | 514/21 |
| 5,830,859 A * | 11/1998 | Schmidt | 514/12 |
| 5,916,553 A | 6/1999 | Schmidt | |
| 5,932,207 A * | 8/1999 | Schmidt | 424/85.1 |
| 5,980,252 A * | 11/1999 | Samchukov et al. | 433/215 |

FOREIGN PATENT DOCUMENTS

| | | |
|---|---|---|
| CN | 2 286 032 | 7/1998 |
| EP | A-0 361 896 | 4/1990 |
| EP | A-0 366 029 | 5/1990 |
| EP | 0 615 428 | 3/2002 |
| GB | A-2 164 042 | 3/1986 |
| GB | 2215209 A | 9/1989 |
| JP | A-60 253455 | 12/1985 |
| JP | A-1 161461 | 6/1989 |
| JP | A-2 249556 | 10/1990 |
| JP | A-7 008547 | 1/1995 |
| JP | 7 504837 | 6/1995 |
| JP | A-7 171211 | 11/1995 |
| JP | A-8 332217 | 12/1996 |
| JP | 10-99356 | 4/1998 |
| JP | 10-328217 | 12/1998 |
| RU | 1 818 091 | 5/1993 |
| RU | 2 025 132 | 12/1994 |
| RU | 2 062 622 | 6/1996 |
| RU | 2 133 595 | 7/1999 |
| WO | WO 84/00540 | 2/1984 |
| WO | WO 87/06120 | 10/1987 |
| WO | WO 88/07078 | 9/1988 |
| WO | WO 90/00060 | 1/1990 |

OTHER PUBLICATIONS

File Caplus on STN, DN No. 130:92004. Labes et al. 'A Novel Phosohatase Regulating Neurite Extension on CNS Inhibitors', Mol. Cell. Neurosci. vol. 12, No. 1/2, pp. 29-47. Abstract only, 1998.*

File Caplus on STN, DN No. 115:156383. Tetzlaff et al. 'Response of Facial and Rubrospinal Neurons to Axotomy', J. Neurosci. vol. 11, No. 8 pp. 2528-2544. Abstract only, 1991.*

Editorial—Critical Factors Controlling Angiogenesis: Cell Products, Cell Matrix, and Growth Factors, Laboratory Investigation, vol. 55, No. 5, 1986, pp. 505-509.

(Continued)

Primary Examiner—Anish Gupta
(74) Attorney, Agent, or Firm—Blank Rome LLP

(57) ABSTRACT

The invention concerns a means for the at least partial production of reproduction of biological parts, especially or organs for living beings in which a carrier with an active ingredient complex is coated or in which the carrier contains an active ingredient complex, and the active ingredient complex has the following components, which are difference from one another and are specifically suited to each biological part to be produced, in the form of at least one structural component on the basis of extracellular material specifically suited to the cells of each of the biological parts to be produced, at least one recruiting component, at least one adhesion component, and at least one growth and/or maturation component. The method according to the invention can be used for the production, reproduction, or stabilization of vertebral structures; to treat osteoporosis, psuedoarthrosis, and bone defects; to fill large bone defects; and to heal endoprostheses.

27 Claims, 2 Drawing Sheets

OTHER PUBLICATIONS

Figure 1:
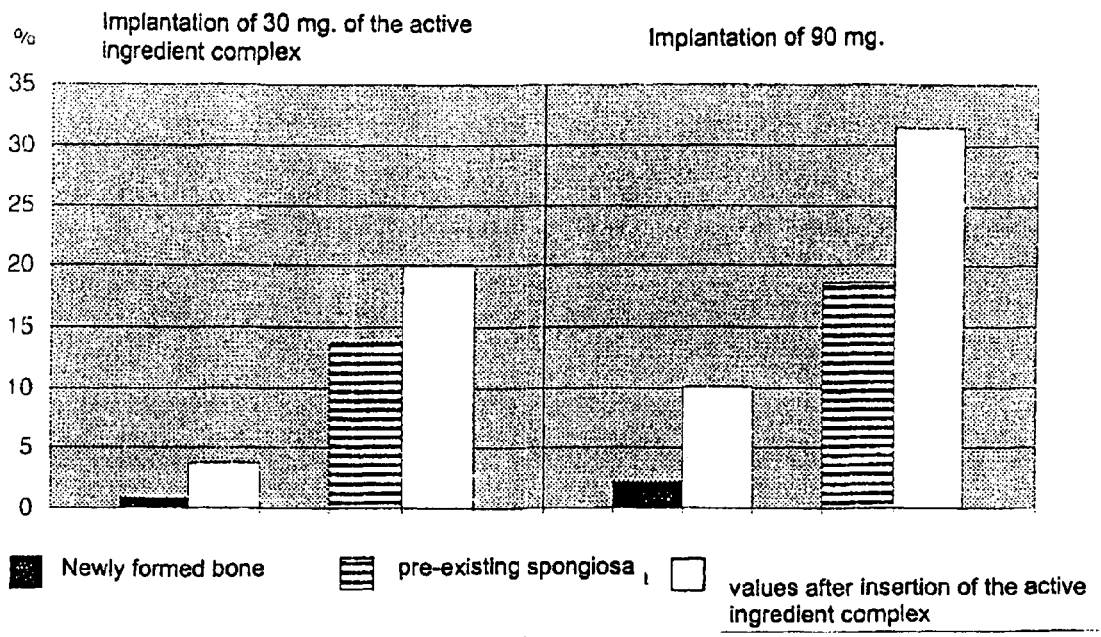

K. Anselme—Osteoblast Adhesion on Biomaterials—Biomaterials, GB, Elsevier Science Publishers BV., Barking, Bd. 21, Nr. 7, Apr. 2000, pp. 676-675.
Article: Data from Medline and Journal of Cell Biology (4 pages).
Heumann et al., Medical Sensation from a Tubingen researcher, May 1989, pp. 1-14 (Germany w/English translation).

Dijke et al., Growth Factors for Wound Healing, Bio/Technology, vol. 7, 1989, pp. 793-798.
Laminin, Fibronectin and Other Multiadhesive Matrix Glycoproteins, Chapter 23, Multicellularity:Cell-Cell and Cell-Matrix Interactions, pp. 920-924.

* cited by examiner

AGENT FOR THE MANUFACTURE OF BIOLOGICAL PARTS INCLUDING AN ACTIVE INGREDIENT COMPLEX AND CARRYING MATERIALS SUITABLE FOR THE ACTIVE INGREDIENT COMPLEX

This is a continuation-in-part of application Ser. No. 08/899,270, filed Jul. 23, 1997, now U.S. Pat. No. 5,298,635 which was a FWC of application Ser. No. 08/313,113, filed Dec. 7, 1994, which claims priority of Ser. No. 07/849,083, filed Sep. 17, 1992, which claims priority of German Patent No. WO 91/07324 and this is a continuation-in-part of Ser. No. 08/350,666, filed Dec. 7, 1994, which claims priority from Ser. No. 08/474,150, filed Jul. 7, 1995, which claims priority from U.S. Pat. No. 5,830,859, issued Nov. 3, 1998 all of which are herein incorporated by reference.

BACKGROUND OF THE INVENTION

The invention is concerned with means for the at least partial production or reproduction of biological parts, especially of organs for living-beings, which contains, among other things, an active ingredient complex with the following components, which are different from one another and are specifically suited to each biological part to be produced, in the form of at least one structural component on the basis of extracellular material specifically suited to the cells of each biological part to be produced, at least one recruiting component, at least one adhesion component, and at least one growth and/or maturation component.

In the prior art, an active ingredient complex for the production of biological parts, especially of organs for living-beings, with the mentioned components is already known. In this known active ingredient complex, the structural component can consist, for example, of various types of collagen, elastin, or proteoglycans. As recruiting component for this active ingredient complex, especially chemotactic substances should be mentioned, for example, peptides such as N-F-Met-Leu-Phe- and/or metabolites of arachidonic acid such as leukotrienes.

Proteins of the type of fibronectin or laminin, but also cell-adhesion molecules such as L-CAM, N-CAM, and matrix-adhesion molecules such as cytotactin, tenascin, collagen types IV, V, and VII, synthetic peptides, and transmembrane compound proteins such as integrin can be used as adhesion components. The examples for adhesion components that were mentioned first—fibronectin and laminin—are to be classified in the area of matrix-adhesion molecules for the purposes of the active ingredient complex explained here. As additional components, the active ingredient complex mentioned shows (or comprises) at least one growth and/or maturation component, preferably in the form of one or several cytokines. Examples of such cytokines are the colony-stimulating factors for the production of blood, the fibroblast growth factor for the production of connective tissue, the epidermal growth factor for the production of skin, the cartilage inducing factor for the production of cartilage, the lymphocyte-activating factor as well as spleen peptides for the production of the spleen or the lymph nodes, the T-cell growth factor as well as thymus peptides for the production of thymus, the bone growth factor as well as the transforming growth factor for the production of bones, and the angiogenesis factor for the production of blood vessels. Moreover, the following cytokines are used: interleukins, insulinlike growth factors, tumor-necrosis factor, prostaglandins, leukotrienes, transforming growth factors, growth factor derived from platelets, interferons as well as growth factor derived from endothelial cells.

The details of this active ingredient complex can be taken from German patent DE 39 36 568.9, whose disclosure is expressly included herewith.

In order to be able to be used for the production or reproduction of biological parts, the active ingredient complex must be available in highly purified form. The production of this active ingredient complex is thus both time-consuming and expensive. For example, when using this active ingredient complex to fill up bone defects with bones, one needs an amount of the active ingredient complex that fills up the entire bone defect. The fact that the active ingredient complex is highly effective, but nonetheless very expensive, is therefore a disadvantage.

If larger bone defects are to be filled, the inserted implant that consists of the active ingredient complex must also have a sufficient mechanical stability of its own so that it is not compressed by the surrounding soft tissue. The active ingredient complex after its production has a cotton-like consistency. For this reason, the application mentioned either must be compressed—which leads to a higher mechanical stability, but also to excessive consumption of material—or a sufficiently stable carrier must be employed together with the active ingredient complex. The combination of a carrier with the active ingredient complex is, however, hardly free of problems. According to the existing knowledge on the active ingredient complex and its complex mode of action, one should be concerned at least about a hindrance of the formation or reproduction of each of the biological parts to be treated, e.g., the regeneration of bone. The risk of a reaction toxic to the tissue was also suspected.

Moreover, applications of the active ingredient complex in disorders or defects have not been possible if the implants consisting of the active ingredient complex are subject to such high mechanical stresses that even the mechanical stability of a compressed material does not suffice.

SUMMARY AND ADVANTAGES OF THE INVENTION

Taking this as the starting point, the present invention is thus based on the technical problem of preparing a less expensive means that at the same time exhibits strong mechanical stability.

The problem is solved by a means in which a carrier is coated with the active ingredient complex mentioned or by a means that contains the active ingredient complex.

The solution to the problem has not been obvious for that reason alone that, as already mentioned, it is quite problematic to provide a combination of the active ingredient complex with a carrier coated with the active ingredient complex or one containing it, because the healing activity of the active ingredient complex, for instance in a bone defect, may be disturbed or at least may be complicated by possible immune reactions.

Certain requirements are made on possible carriers. Carrier materials that can be used are, in principle, those that are moldable and that have—at least at the beginning—a desired stability of form and dimension, whereby a controlled loss of form and stability can result after being implanted in the organism. For certain applications they must, moreover, be completely absorbable and may, in principle, have only a low toxicity. This goes not only for the carrier material itself, but also for its decomposition products. In this connection by the term toxicity is meant not only an acute toxic tissue reaction, but also subacute effects which include, e.g., carcinogenic and immunologic effects. The carrier combined with the active ingredient complex according to the invention can consist of polymer, ceramic, metallic, or nonmetallic carrier materials. In the case of polymer carrier materials, especially polymers made from natural monomers such as polyamino acids (polylysine), polyglutamic acid, etc., and polymers of lactic acid can be taken into consideration. Copolymers, e.g., made of polylactic acid and hydroxyacetic acid, can also be used.

Polylactates are polyesters of lactic acid with the chemical formula:

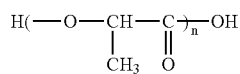

During the direct polymerization of monomers, polymers with relatively low molecular weights result. The upper limit lies at about 20,000 Da. Higher molecular weights can occur by combining cyclical dimers at high temperatures, low pressure, in the presence of catalysts converters. The lactic acid polymers are biodegradable, biocompatible, water insoluble, and they are distinguished by a strong stability.

In addition, different collagens can be used as carrier materials. In this connection especially collagens of type I, IV, V, and VII should be mentioned. The collagens can be used, for example, in the form of fleeces or gels, and they display especially good immunologic compatibility in conjunction with problem-free processing.

Among the ceramic carrier materials that should be mentioned are especially glass ceramics, in particular, calcium phosphate ceramics, aluminum oxide ceramics, and hydroxylapatite ceramics.

The calcium phosphate ceramics are based on the CaO/$P_2O_5$ system. On the basis of this system five different binary compounds exist. In this connection tricalcium phosphate (TCP) and tetracalcium phosphate have proven themselves as a suitable carrier material for the purposes of the present invention.

TCP is produced by pressing and then sintering the raw materials calcium oxide (CaO) and diphosphorus pentoxide ($P_2O_5$). Alternatively, it can also be produced in one step by hot pressing. Carrier materials produced from TCP can be used in the form of plates or disks and as granulates.

Tetracalcium phosphate is produced like TCP in two steps, first by concentrating the raw materials at intervals of 5 to 10 μm in the crystal lattice and then the substance in calcined at 1110 to 1500° C.

Hydroxylapatite is produced through the ceramic calcining of pentacalciumhydroxide triphosphate powder at 1250°. Moreover, a natural material, such as the carbonaceous skeleton of red algae, can also be used in the production of a hydroxylapatite ceramic. In so doing and after first washing and drying, the organic components are removed by pyrolysis at a temperature of about 700° C. Then the transformation to hydroxylapatite occurs by adding phosphate solution at increased pressure and increased temperature.

In another method of producing a hydroxylapatite ceramic that starts with the natural skeleton of corals, the calcium carbonate of the corals is transformed into hydroxylapatite or a mixture of hydroxylapatite and other mineral structures through hydrothermal conversion. In the material that results, the coralline structure remains intact, i.e., especially the interconnecting pore system of the corals.

Aluminum oxide ceramics, which are polycrystalline in structure, contain up to about 99.7% aluminum oxide and a small share of magnesium oxide and/or zirconium oxide. After precompressing under high pressure, they are sintered to a solid body at temperatures of about 1500–1800° C. For the purposes of the present invention microporous aluminum oxide ceramics are used. Monocrystalline forms (sapphires) can also be used.

As further examples, the so-called ionic polymers—for which the designation "ionomer," which will also be used here, is customary—can be used as carrier materials. In this connection, for example, ionomer cement, should be mentioned, which is produced through the reaction of glass powder with a polyalkene acid. In a modification, calcium carbonate, acting as a foaming agent, can also be added to the glass powder. During the reaction of the glass powder and the calcium carbonate mixed with the polyalkene acid $CO_2$ is released, which causes the porosity.

Ionomer cement is in principle a two-component system and is formed through the reaction of a glass powder (calcium, aluminum, fluoride, silicate glass) with a polyalkene acid (high molecular mixed polymerizate of maleic acid and acrylic acid). The course of the cement-forming reaction is initiated by the action of the polyalkene acid on the basic glass particles. In so doing water serves as the reaction medium. In addition to the polyalkene acid the fluid component of the reaction system consists of tartaric acid. By using this tartaric acid, the speed at which the cement sets can be controlled.

Ionomer cement is deemed compatible with tissue and is permanently stable in a biological environment. It is, moreover, subject to plastic deformation. The ionomer cement used for the purposes of the present invention is free of additives in the form of pigments, dyes, or metallic salts. It is, in addition, free of monomeric, unsaturated carbonic acids such as, e.g., acrylic acid and maleic acid, and is used sterile and free of pyrogens.

Above all titanium, also in the form of alloys, is among the metallic carriers that should be mentioned. In this connection especially an alloy made of components of titanium, aluminum, and vanadium, were investigated. The metallic carriers can be used in the form of laminae, which can also display a lattice structure, or also in the form of cylindrical hollow bodies with a lattice structure.

Additional metallic carrier materials are available in the form of endoprostheses, which, when coated and/or filled with the active ingredient complex, allow the endoprostheses to grow more quickly and permanently into the organism.

The endoprostheses thus form a special type of carrier according to the invention. By accelerating growth into the implanted site and at the same time improving growth one can in turn bring about longer durability and longer and earlier use of the endoprostheses.

Carbon, which can be used in the form of so-called "carbon cages" that form cylindrical hollow bodies, should be mentioned above all else as a nonmetallic carrier. Both the titanium (hollow) bodies and the carbon cages are filled with the active ingredient complex, while the other carrier materials available in the form of lamellae or granulates are usually coated with the active ingredient complex.

The titanium bodies and carbon cages mentioned can, when filled with the active ingredient complex, be used for the production, reproduction, or stabilization of vertebral structures. This allows for the unique possibility of correcting defects in vertebrae of recovering destroyed vertebrae of the spinal column. With the active ingredient complex used until now this was not possible because it could not withstand the mechanical stress inside the spinal column. The hollow bodies or cages filled with the active ingredient complex create the mechanical stability without bringing on immunological counter-reactions or worsening the effectiveness of the active ingredient complex.

Moreover, the means according to the invention can be used to treat osteoporosis, pseudoarthrosis, and bone defects and to fill large bone defects and heal endoprostheses.

Among the bone defects that can be treated successfully with the means according to the invention are, e.g., the chain of auditory ossicles, the reconstruction of the frontal sinus, and the top of the ethmoid bone; and it can be used as a dental implant.

DETAILED DESCRIPTION OF THE PREFERRED EMBODIMENTS (BEST MODE)

Below the invention will be illustrated in greater detail by using examples.

I. Production of the Active Ingredient Complex

In the following the essential steps of the production of the active ingredient complex are described.

The long bones of calves, sheep, rabbits, or rats are cleaned; among other things, they have the bone marrow removed and then are frozen. The frozen bones are crushed to a particle size of less than 2 mm. The fat is removed from the crushed pieces of bone by placing it in acetone and decalcified in 0.6 N hydrochloric acid. After that it is lyophilized, and one obtains a demineralized bone matrix, which is extracted in a 4-molar guanidine-HCL solution. The extracted solution is dialyzed against distilled water and the active ingredient complex is obtained in the precipitate by centrifuging off and lyophilizing.

This fundamental method of production is represented again in the flow diagram below.

Diagram 1: Flow Diagram of the Production of the Active Ingredient Complex

Diaphyses of long bones fresh from the slaughter house
Grounding to a particle size (<2 mm)
Fat removed in acetone I Decalcified in 0.6 N HCL
Washed and lyophilized
Demineralized bone matrix
Extraction in 4 M GuHCl
Residue Excess
Dialysis in distilled H2O
I Precipitate contains the active ingredient complex Ii. Effectiveness of the Active Ingredient Complex without Using the Carrier Materials To show that the active ingredient complex is effective in itself, first an experiment is represented in which the active ingredient complex is implanted without additional carrier materials.

1. Animals Used for the Experiment

Female rabbits of the chinchilla breed having an average body weight of 3,089 g. are used. They received food for rabbits and tap water that was acidified with hydrochloric acid to a pH of 4.5 and twice ozonized according to need.

The animals were anesthetized by subcutaneous injection with a mixture of Ketamin and xylazin.

2. Preparation of a Bone Defect in the Rabbits

Using an internally cooled drill, an implant layer having a 4-mm diameter and a thickness of about 9 mm is prepared in the knee joint (distal femur end) of the rabbit. Then the drill hole formed in this way is filled with 30 mg. and 90 mg. of the active ingredient complex, which was produced as described in section I. In each case an additional drill hole serves in the form of an "empty hole" to control the new formation of bone.

FIG. 1 shows the new formation of bone in the empty hole and in the drill hole after implantation of the active ingredient complex, as well as the thickness of the surrounding, pre-existing spongiosa 28 days after the operation (n=2/amount of active ingredient).

When evaluating the experiments it was determined that the density of the spongiosa surrounding the drill holes after implantation of 30 mg. of the active ingredient complex was 45% higher than the empty hole and the one with 90 mg. of the active ingredient complex was 69% higher than that of empty hole. In this connection the amount of pre-existing spongiosa had no influence at all on the regeneration in the defect, for the formation of new bone after the insertion of the active ingredient complex did not originate from the drill hole periphery, but was evenly distributed over the defect.

III. Formation of Bone in the Lower Jaw of Sheep when Using Tricalcium Phosphate (Tcp)

1. Animals Used for the Experiments

For the experiments described below full-grown domestic sheep from the Viehzentrale Südwest AG in Stuttgart were used. They received hay and water as food, as well as a mush of Altromin pellets three days before the operation.

The animals were premedicated with 1 ml xylazin/1 ml Ketanest I.M. Then the sheep were anesthetized with Nembutal.

2. Preparation of the Implants

TCP was suspended in a solution of 100 mg. of the dissolved active ingredient complex with 10 ml. of water and deep frozen in liquid nitrogen while constantly stirring. After lyophilizing 24 hours and subsequent gas sterilization (ethylene oxide), the TCP doped with the active ingredient complex was inserted into the lower jaw defect of a sheep, as described below. Moreover, another lower jaw defect, which served as a comparison, was filled with TCP without the active ingredient complex and sterilized in the autoclave.

3. Preparation of the Lower Jaw Defect in a Sheep

In a correspondingly prepared lower jaw of a sheep a standardized bone cylinder is cut out and removed by using a trepan drill with a 5-mm diameter and while cooling with physiological salt solution. Then one of the drill holes formed in this way was filled with TCP that was doped with the active ingredient complex in accordance with the experiment's specification 1, and the second drill hole was filled with TCP without the active ingredient complex.

Figure 2:
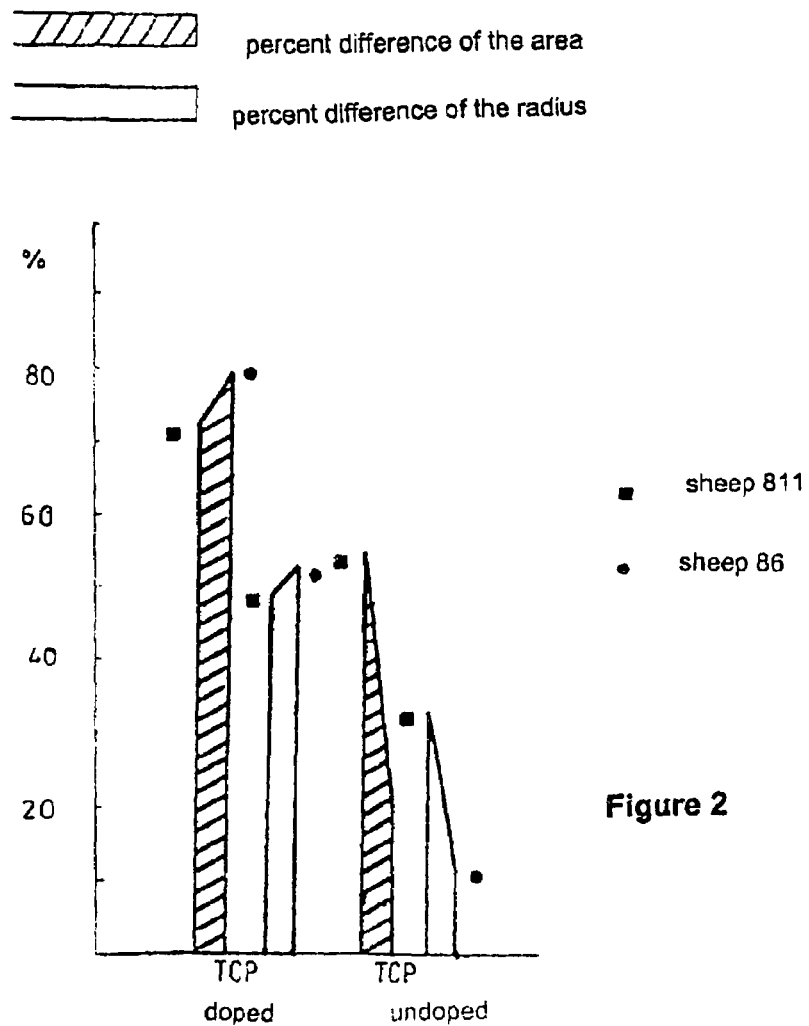

The results of the bone growth in the lower jaw defects are graphically represented in FIG. 2 to provide an easy overview. The experiment lasted 26 and 41 days, respectively.

It was shown that by doping the TCP with the active ingredient complex, a 100% acceleration of the bone regeneration of the lower jaw defect in both sheep no. 811 and no. 86 was reached in the beginning phase. After 41 days the increase in the acceleration of the bone regeneration was still at 10%. The bone healing thus occurred much more quickly in the beginning than without the osteoproductive effects of the implants doped with the active ingredient complex.

This result is Of significance especially for the coating of endoprostheses with the active ingredient complex. An endoprostheses coated with the active ingredient complex, as for example, in the case of a fracture of the neck of the femur, accordingly enables the prosthesis to grow in the tissue more quickly, thus promoting the quicker regeneration and convalescence of each of the patients. In this way the length of stay in the hospital is shortened.

IV. Experiments with Collagens as Carrier Materials

The active ingredient complex that is already known and that was explained above can be used to treat osteoporosis, pseudoarthrosis, and the healing of endoprostheses and to fill up large bone defects. The quantitative return of the active ingredient complex during production that has the required degree of purity is very small. For this reason it was investigated whether carrier materials exist that can be combined with the active ingredient complex so that the active ingredient complex required for each objective can be reduced without at the same time reducing the bone-forming efficacy.

1. Active Ingredient Complex

The active ingredient complex used for the purposes of the experiments described below was produced exactly as described in section I, except that long bones of calves were used.

2. Experiment of Animals

Male Wistar rats weighting between 350 and 400 g. were used and held in an airconditioned stall at 23° C. with a relative humidity of about 50%. They were fed a diet for rats and mice.

Each animal that was tested was implanted with two implants with the same carrier material in the abdominal wall musculature—one of which was coated with the active ingredient complex and the other of which served as the comparison implant and was uncoated. The animals were killed after 21 days and the involved areas of the implant in the abdominal wall musculature removed and histologically evaluated.

3. Carrier Materials Used

For these experiments commercially available collagen materials. Collagen A was a pure, sterile, untreated, resorbable cattle hide collagen, which is free of any foreign additives such as stabilizers or disinfection agents.

Collagen B was a purified, lyophilized, lightly cross-linked, sterile, and nonpyrogenic cattle hide collagen with weak antigenic properties. The helical structure of the collagen remains intact.

Collagen C consists of pure, untreated, resorbable cattle hide fibrils.

Figure 3:
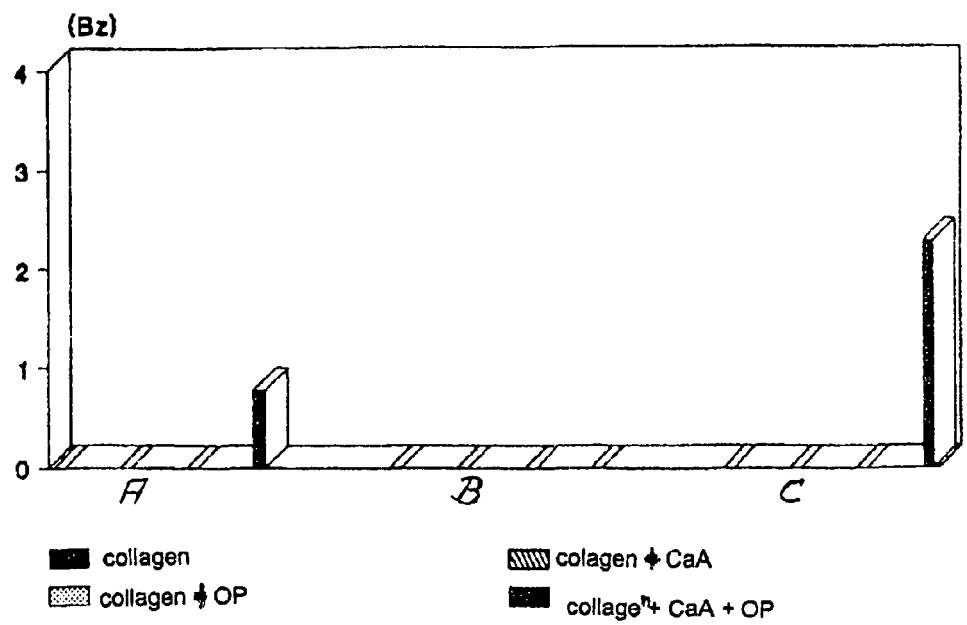

All collagens used were in the form of fleece. Collagen fleece pieces were cut to 50 mg each, and 1 ml of the solution of the active ingredient complex solution (3 mg/ml) was added to each. In the control implants 1 ml of distilled water was added instead. The collagen fleece pieces treated in this way were frozen at −201 C, lyophilized, and yielded implants with a diameter of about 10 mm and a thickness of about 5 mm. FIG. 3 shows the results of the bone formation of the collagen implants A, B, and C—after 21 days—with and without coating with the active ingredient complex in (cyclosporine A) immune-suppressed animals and in non-immunesuppressed animals. In this connection the evaluation mark (BZ) corresponds to the arithmetical mean of the evaluation marks from three independent persons with six implants for each group.

While collagen A coated with the active ingredient complex showed a boneforming effect in immune-suppressed animals after the time period, the effect could not be proven with collagen B. On the other hand, collagen C showed a very pronounced bone-forming effect.

IV. Test of the Biocompatibility of the Carrier Materials

In tests concerning the improvement of the long-term stability of endoprostheses, small titanium plates with different roughnesses (100, 20, and 0.5 μm a TiAl6V4 alloy (0.5 μm), $Al_2O_3$ plates of the Friedrichsfeld firm, and small hydroxylapatite plates from Feldmühle AG were used.

The coatings with the active ingredient complex, which was produced by the general procedures specified above, was applied by the coating method called "dip coating." By dip coating is meant a coating method in which the object to be coated—here the small plates—is dipped into a solution with a desired prespecified concentration of the coating agent—here the active ingredient complex. Then they are lyophilized. Thin coatings or layers are obtained. The test of the specified materials for biocompatibility was carried out with respect to the roughness of the surfaces (n=20; four small plates at a time).

TABLE 1

| Carrier Material | No. of living cells/$cm^2$ | No. of dead cells/$cm^2$ |
|---|---|---|
| hydroxy-lapatite | | |
| 0.2–0.5 μm | 1792 ± 700 | 200 ± 37 |
| 20 μm | 7469 ± 2614 | 2238 ± 715 |
| 50 μm | 4477 ± 408 | 1692 ± 427 |
| Osprovit (Feldmühle) titanium | 7930 ± 2007 | 1638 ± 377 |
| 0.5 μm | 11377 ± 2538 | 1054 ± 308 |
| 20 μm | 9600 ± 3038 | 1754 ± 439 |
| 100 μm | 2308 ± 669 | 2085 ± 623 |
| $TiAl_6V_4$ | | |
| 0.5 μm | 7200 ± 1062 | 2800 ± 954 |
| $Al_2O_3$ highly purified, polished | 11446 ± 1500 | 2292 ± 600 |

In this biocompatibility test of the examined materials it was shown that titanium is very suitable as a carrier material due to the high number of living cells and the best ratio of living to dead cells. While hydroxylapatite produced a similarly good result, TiAl6V4 did considerably worse.

In general it was shown with respect to the surface roughness that, except for $TiAl_6V_4$, the smoothest surfaces (0.2–0.5 μm) produced the best results. As the roughness increases, both the number of living cells and the ratio of living to dead cells fall.

The results of these tests can now be applied to the coating of endoprostheses with the active ingredient complex and also to the coating of dimensionally stable cages.

Before inserting each endoprostheses they are coated with the active ingredient complex in accordance with the dip-coating method and, in addition, the active ingredient complex is inserted into the inner hollow spaces of each prosthesis shaft that has outlets to the shaft surface. Thus, in the event of a possible future loosening of the endprostheses, this provides the advantage that the active ingredient complex can be applied later without a large operation and leads to the formation of bone and thus the anchoring of the endoprostheses.

That the coating with the active ingredient complex leads to higher stress potentialities in comparison with the non-coated surfaces is shown in table 2 using the example of hydroxylapatite (HA). In this connection the tensile strengths on the boundary areas of different implant materials were determined in N/mm²±standard deviation. Hydroxylapatite produced by using hot isostatic presses (HIP), in relation to the hydroxylapatite that was coated with the active ingredient complex, was determined as the material. The implant material was implanted in the distal femur of the rabbit and tested after 84 days. The tensile strengths that were determined are given in the table below.

TABLE 2

| Material | RT (μm) | Days | n | Tensile Strength |
|---|---|---|---|---|
| HA HIP | 0.5 | 84 | 10 | 1.53 ± 0.24 |
| HA HIP WK | 0.5 | 84 | 6 | 2.27 ± 0.31 | n = no. of implants
WK = coating with the active ingredient complex
HIP = hot isostatic presses
RT = surface roughness V. Titanium Bodies and Carbon Cages After the tests represented in section IV proved the basic biocompatibility of titanium, there was a special promise for applying the complex of active substances in dimensionally stable cages made of titanium to interlock vertebral structures. Moreover, so-called carbon cages have proved suitable for this purpose. Interlocking vertebral structures is often necessary when the load-bearing capacity of the spinal column has been impaired by degenerative processes of the intervertebral disks, tumors, or metastases in the spinal column or by osteoporosis so that either vertebral fractures or nerve lesions are a threat. In these cases it is necessary to guarantee the continuity of the spinal column through a mechanically stable implant such as titanium or carbon cages. Until now the necessary bony bridge could be attempted only by obtaining autologous spongiosa in a second operation—which brings with it a series of problems such as the second operation and the risk associated with it, the limited amount of obtainable spongiosa, and complications at the site of removal such as infections or chronic pain.

By filling the titanium bodies or carbon cages with the active ingredient complex, a bony bridge could be guaranteed in a short time without requiring autologous spongiosa. In this connection both the titanium bodies and the carbon cages are constructed as hollow bodies with a lattice structure. These latticed structures allow for a quick vascularization even in the inside of the dimensionally stable components so that the active ingredient complex can develop its activity and the bone formation penetrates into the entire required area without mechanical forces jeopardizing the newly formed bones. In addition to the use in the area of vertebral structures, such a titanium body or carbon cage can also be used for other desired implant types, as, for instance, in the jaw or in long bones.

Figure 4:

A titanium body filled with the active ingredient complex is represented in FIG. 4.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

To the Figures:

FIG. 1:

| Implantation of 30 mg. of the active ingredient complex | | Implantation of 90 mg. | |
|---|---|---|---|
| Newly formed bone | pre-existing spongiosa | values after insertion of the active ingredient complex | |

FIG. 3:

| collagen | colagen = CaA |
|---|---|
| collagen = OP | collage + CaA + OP |

FIG. 2:

percent difference of the area
percent difference of the radius

| | sheep 811 |
| | sheep 86 |
| doped | undoped |

The invention claimed is:

1. A composition comprising a carrier selected from the group consisting of polymer, ceramic, metallic and nonmetallic materials; and an active ingredient complex, said active ingredient complex comprising at least one bone derived structural component, at least one bone derived chemotactic component, at least one bone derived adhesion component, and at least one bone derived growth or maturation component.

2. A composition according to claim 1, wherein the ceramic carrier materials are selected from the group consisting of hydroxylapatite, calciumphosphate, aluminum oxide, and ionomer cement.

3. A composition according to claim 1, wherein the metallic carrier material is titanium or titanium alloy.

4. A composition according to claim 1, wherein the nonmetallic carrier material is carbon.

5. A composition according to claim 1, wherein the polymer is derived from natural monomers taken from the group consisting of amino acids, glutamic acid, lactic acid, hydroacetic acid, and copolymers thereof.

6. A composition according to claim 1, wherein the polymer is a polylactate.

7. A method of stabilizing vertebral structures or treating broken vertebral structures or fixing endoprosthesis comprising the step of implanting a composition according to claim 1 into living beings.

8. A method according to claim 7, wherein the metallic carrier material is titanium or a titanium alloy.

9. A method according to claim 7, wherein the nonmetallic carrier material is carbon.

10. A method according to claim 7, wherein the ceramic carrier materials are selected from the group consisting of hydroxylapatite, calciumphosphate, aluminum oxide, and ionomer cement.

11. A method according to claim 7, wherein the carrier is an endoprosthesis.

12. A method of treating osteoporosis and pseudoarthrosis or of filling bone defects comprising the step of implanting a composition according to claim 1 into living beings.

13. A method according to claim 12, wherein the ceramic carrier materials are selected from the group consisting of hydroxylapatite, calciumphosphate, aluminum oxide, and ionomer cement.

14. A method according to claim 12, wherein the metallic carrier material is titanium or a titanium alloy.

15. A method according to claim 12, wherein the nonmetallic carrier material is carbon.

16. A method according to claim 12, wherein large bone defects are filled.

17. A method according to claim 12, wherein the polymer is derived from natural monomers taken from the group consisting of amino acids, glutamic acid, lactic acid, hydroacetic acid, and copolymers thereof.

18. A method according to claim 17, wherein the polymer is a polylactate.

19. A method according to claim 12, wherein the polymer is derived from natural monomers taken from the group consisting of amino acids, glutamic acid, lactic acid, hydroacetic acid, and copolymers thereof.

20. A method according to claim 19, wherein the polymer is a polylactate.

21. A composition according to claim 1, wherein the carrier comprises a lattice structure for receiving the active ingredient complex therein.

22. A method according to claim 7, wherein the carrier comprises a lattice structure for receiving the active ingredient complex therein.

23. A method according to claim 12, wherein the carrier comprises a lattice structure for receiving the active ingredient complex therein.

24. A composition according to claim 1, wherein the carrier is collagen coated with the active ingredient complex.

25. A method according to claim 7, wherein the carrier is a collagen coated with the active ingredient complex.

26. A composition according to claim 1, wherein said growth or maturation component is a cytokine.

27. A method according to claim 7, wherein said growth or maturation component is a cytokine.

\* \* \* \* \*